US006294193B1

(12) United States Patent
Cody

(10) Patent No.: US 6,294,193 B1
(45) Date of Patent: Sep. 25, 2001

(54) PLANTAGO MAJOR AND HYPERICUM PERFORATUM COMPOUND FOR USE IN TREATING A TOBACCO OR NICOTINE HABIT

(76) Inventor: Mary E. Cody, 15 Meadowbrook Rd., Boonton Township, NJ (US) 07005

( * ) Notice: Subject to any disclaimer, the term of this patent is extended or adjusted under 35 U.S.C. 154(b) by 0 days.

(21) Appl. No.: 09/524,711

(22) Filed: Mar. 14, 2000

Related U.S. Application Data

(62) Division of application No. 09/073,463, filed on May 6, 1998, now Pat. No. 6,063,401.

(51) Int. Cl.[7] .............................. A61K 9/20; A61K 9/28; A61K 9/48
(52) U.S. Cl. .................. 424/451; 424/464; 424/474; 424/479
(58) Field of Search ................... 424/451, 464, 424/456, 474, 195.1, 479, 489, 455, 453, 452

(56) References Cited

U.S. PATENT DOCUMENTS

| | | | |
|---|---|---|---|
| 4,284,089 | 8/1981 | Ray | 131/270 |
| 4,744,988 | 5/1988 | Brox | 424/456 |
| 4,821,745 | 4/1989 | Rosen et al. | 131/270 |
| 4,839,174 | 6/1989 | Baker et al. | 424/447 |
| 4,888,239 | 12/1989 | Brox | 428/402.2 |
| 4,908,213 | 3/1990 | Govil et al. | 424/447 |
| 4,920,989 | 5/1990 | Rose et al. | 131/270 |
| 4,943,435 | 7/1990 | Baker et al. | 424/448 |
| 4,953,572 | 9/1990 | Rose et al. | 131/270 |
| 5,016,652 | 5/1991 | Rose et al. | 131/270 |
| 5,135,753 | 8/1992 | Baker et al. | 424/435 |
| 5,162,037 | 11/1992 | Whitson-Fischman | 600/12 |
| 5,431,916 | 7/1995 | White | 424/451 |
| 5,641,512 | 6/1997 | Cimiluca | 424/455 |
| 5,716,635 | 2/1998 | Cody | 424/447 |

FOREIGN PATENT DOCUMENTS

| | | |
|---|---|---|
| 1911112 | 9/1970 | (DE) . |
| 9632117 | 10/1996 | (WO) . |
| 9713489 | 4/1997 | (WO) . |
| 9742963 | 11/1997 | (WO) . |

OTHER PUBLICATIONS

Medical Economics Company, Inc., Physician's Desk Reference, Copyright 1998, p. 1139–1144.

William Boericke, M.D., Pocket Manual of Homoeotaphic Materia Medica comprising The Characteristics and Guiding Symptoms of all Remedies, date unknown, p. 521–522.

*Primary Examiner*—James M. Spear
(74) *Attorney, Agent, or Firm*—Cantor Colburn LLP

(57) ABSTRACT

A composition containing the herbs *Plantago major* and *Hypericum perforatum* is presented. Use of the composition, of the present invention, in a form adapted to be orally ingested produces a diminished desire for tobacco (i.e., nicotine) without the use of nicotine itself and provides an anti-depressive effect.

3 Claims, No Drawings

PLANTAGO MAJOR AND HYPERICUM PERFORATUM COMPOUND FOR USE IN TREATING A TOBACCO OR NICOTINE HABIT

CROSS REFERENCE TO RELATED APPLICATIONS

This application is a divisional application of U.S. patent application Ser. No. 09/073,463, filed on May 6 1998 and granted as U.S. Pat. No. 6,063,401 on May 16, 2000, which is herein incorporated by reference in its entirety.

BACKGROUND OF THE INVENTION

1. Field of the Invention

The present invention relates generally to an aid for use in treating a tobacco or nicotine habit. More particularly, the present invention relates to a composition containing as an active ingredient the herbs *Plantago major* and *Hypericum perforatum* for use as an aid in controlling a tobacco (i.e., nicotine) habit.

2. Brief Discussion of the Related Art

The U.S. Surgeon General has determined that cigarette smoking is a major risk factor in coronary artery disease and is the cause of approximately 30% of all cancer deaths. Tobacco chewing has been shown to cause cancers of the mouth and throat. Because of the undesirable effects of tobacco smoking or tobacco chewing, many devices have been developed as aids for treatment of the tobacco and nicotine habit. For example, in a simulated smoking device, the tobacco therein is heated rather than burned, releasing nicotine vapor which is then drawn into the smoker's lungs. Thus, the smoker obtains the desired nicotine, but without also ingesting the full range and concentration of harmful products of burning tobacco. One such simulated smoking device using a source of vaporizable nicotine is disclosed in U.S. Pat. No. 4,284,089 issued to Ray. Other simulated smoking devices contain substances which microencapsulate materials that simulate the taste and aroma of tobacco, and which are then released by squeezing or crushing the device. Such devices often do not raise the nicotine level in the blood sufficiently to satisfy the desire for nicotine, and thus are ineffective as aids to stop smoking. Other disadvantages include irritation of the mucosa, which is intolerable to some patients, and the bad taste of nicotine introduced orally.

Alternatively, tobacco concentrates have been processed into tablets or gum which may be sucked or chewed in the mouth of the user, the nicotine being absorbed into the user's body through the lining of the mouth. However, chewing gum formulations suffer from numerous drawbacks. They have a bad taste, they may lead to mouth ulcers and heartburn, they cannot be used effectively by denture wearers, and they depend on the patient following the prescribed chewing regime. Difficulties associated with oral administration include nausea, rapid nicotine degradation, and irregular and unpredictable blood plasma levels. Inability to self-administer the gum while the patient is asleep leads to low or even zero levels of nicotine in the morning and a return of the smoking urge. Even with immediate administration of nicotine gum, it can take up to one hour before effective plasma levels of nicotine are again obtained.

Transdermal patches have also been used as aids in the reduction of incidence of tobacco smoking or chewing. These patches contain tobacco or tobacco by-products, as described in U.S. Pat. No. 4,821,745 issued to Rosen et al, or they contain nicotine, as described in U.S. Pat. No. 4,839,174 issued to Baker et al, U.S. Pat. No. 4,908,213 issued to Govil and Kohlman, and U.S. Pat. No. 4,943,435 issued to Baker et al. Patches containing nicotine have been used in conjunction with gum containing nicotine, as described in U.S. Pat. No. 5,135,753 issued to Baker et al, and in conjunction with an oral aerosol spray as described in U.S. Pat. No. 4,920,989, U.S. Pat. No. 4,953,572, and U.S. Pat. No. 5,016,652, all issued to Rose et al. One disadvantage to using a transdermal patch containing nicotine is that nicotine is a known skin irritant, and transdermal patches containing nicotine often cause pruritus.

In addition to the above-described drawbacks and disadvantages, all of these devices and methods suffer from a reliance on nicotine as an aid in controlling nicotine craving, when nicotine is the addictive agent. The use of nicotine as in aid in controlling nicotine addiction can cause addiction to the gum or patch itself. There is also the potential for increased addiction if the patient continues regular use of tobacco while chewing the gum or wearing the patch. Furthermore, nicotine is a known toxin with profound physiological effects on the body, including increasing blood pressure and heart rate.

The use of herbs in conjunction with transdermal patches is known in the art. A metal-based transdermal patch, applied at an acupuncture point in conjunction with a magnetic field, and containing a homeopathic mixture of at least one herb has been disclosed in U.S. Pat. No. 5,162,037 issued to Whitson-Fischman. The patch described therein has several significant features. The patch is made of a porous material such as sintered metal, and is fitted with a metal sphere or ball made of iron, steel or other ferrous alloy. Furthermore, the patch is applied at appropriate acupuncture sites and subjected to a uniform polar magnetic field. The patch is impregnated with a homeopathic mixture of at least one herb, herbal extract or other component such as pineal gland.

The herb *Plantago major* has been known as a tobacco deterrent (both smoking tobacco and chewing tobacco) for many years, see Materia Medica, Boericke & Runyan, Boericke & Tafel, Inc. Philadelphia, Pa., 1927, pages 521–522. A clinical trial conducted in 1992 at Essex Testing Clinic in Verona, N.J. also found that oral administration of *Plantago major* extract caused an aversion to tobacco in human subjects who were heavy smokers. It is known in the art to place the herb *Plantago major* in a liquid composition or in a solid form, both of which are intended to be orally ingested by a user.

The use of *Plantago major* in transdelmal patches is disclosed in commonly assigned U.S. Pat. No. 5,716,635 issued to Cody. Disclosed is a transdermal patch containing as an active ingredient an extract of the herb *Plantago major* for use as an aid in controlling a tobacco (i.e. nicotine) habit is disclosed. A transdermal patch is impregnated with an extract of *Plantago major* in the form of a layer of gel disposed between an inner permeably layer and an impermeable, non-absorbent outer layer. The concentration of the extract in the gel may be from about 1% by volume to about 100% of the total composition. The transdermal patch is conveniently and privately used on the skin of a user as an to overcoming nicotine addiction.

One of the difficulties is overcoming a tobacco habit is the profound physiological effects of the body when a smoker attempts to stop smoking and experiences a withdrawal from nicotine. Individuals suffering from nicotine withdrawal commonly experience some form of depression which is associated with such withdrawal from an addictive substance. To counter the depressive effects of nicotine withdrawal, pharmaceutical anti-depressants, such as bupropion, are administered to help with such effects. Pharmaceutical anti-depressants are often administered to smokers who are attempting to reduce their addiction to nicotine-containing products, such as cigarettes, cigars, chewing tobacco, etc. The use of pharmaceutical anti-depressants, e.g., bupropion, has a disadvantage in that the user is exposed to the side-effects which are commonly associated with such pharmaceuticals. For example, common side effects experienced during the use of bupropion are the following: (1) the user may experience sexual disfunction; (2) dry mouth; (3) the user is subjected to a level of toxicity due to oral ingestion of the drug and (4) bupropion has mutagenicity effects which can be associated with birth defects. See Physicians' Desk Reference, Medical Economic Company Inc., Montvale, N.J., 1998, pages 1140–1143.

Tobacco aversion, or a reduction in craving, may be accomplished by oral ingestion of compounds which are intended to aid in the cessation of tobacco use. As is known in the related arts, pharmaceutical compounds or other compositions may be dispersed by numerous methods. For example, pharmaceutical or other compositions may be encapsulated within a soft gelatin shell and orally ingested in this form. Soft gelatin capsules, commonly referred to as soft-gels and seamless soft gelatin capsules, are each one piece capsules containing pharmaceutically acceptable actives or other compounds in a liquid or semi-liquid state. These capsules are fashioned, filled and sealed in one continuous operation. Soft gelatin capsules containing liquid pharmaceutical compositions provide an excellent system for the delivery of pharmaceutically acceptable actives. Soft gelatin capsules are a preferred dosage form for accurately dispensing liquids, offering a simple means of masking the unpleasant taste and aromas of many pharmaceutically acceptable actives. Liquid compositions offer several advantages over solid compositions. Liquids are easy to swallow and provide an excellent vehicle for the uniform delivery of pharmaceutical actives. Liquids provide a rapid onset on pharmacologic action, since the composition does not first have to disintegrate and dissolve in the gastrointestinal tract. Additionally, soft gelatin capsules are aesthetically appealing (especially when filled with a transparent liquid) and can be manufactured in a wide variety of sizes, shaped, and colors. The use of soft gelatin capsules in a delivery process for pharmaceutical actives is disclosed in U.S. Pat. No. 5,641,512 to Cimiluca; U.S. Pat. No. 5,431,916 to White; U.S. Pat. No. 4,744,988 to Brox; and U.S. Pat. No. 4,888, 239 to Brox, all of which are incorporated by reference in their entirety. In addition, it is of general knowledge that pharmaceutical actives and/or other compositions may be administered in other forms including but not limited to pills, coated pills, tablets or dragees, wherein these forms comprise a solid blend of the pharmaceutical actives and/or other compositions and carrier materials.

SUMMARY OF THE INVENTION

The above-discussed and other problems and deficiencies of the prior art are overcome or alleviated by the composition of the present invention. In accordance with the present invention, a composition having a *Plantago major* component and a *Hypericum perforatum* component is provided to aid in the cessation of tobacco use. The composition combines the desirable properties of *Plantago major*, i.e., creating an aversion to tobacco and easing anxiety, with the desirable property of *Hypericum perforatum*, an anti-depressive. An important factor in nicotine addiction is the discomfort and difficulty which accompanies the depressive effects associated with a nicotine withdrawal after the tobacco user has ceased consuming nicotine-containing products. In contrast to pharmaceutical anti-depressive compositions, *Hypericum perforatum* is all natural, and has few side effects.

In accordance with the present invention, the *Plantago major* and *Hypericum perforatum* composition is intended to be orally ingested by an individual. The *Plantago major* component and *Hypericum perforatum* component may be prepared in either a dried state or as an extract before being packaged and distributed in a form suitable for oral administration, including but not limited to capsules, pills, coated pills, tablets, dragees, or by other means known in the art. It is also within the scope of the invention that the composition of the present invention may also contain suitable inert solid or liquid carriers which are suitable for oral administration. In contrast to prior art treatments, the present invention uses the herb *Plantago major*, rather than the toxic alkaloid nicotine as an aid to overcoming nicotine addiction. Indeed, *Plantago major* contains only minuscule quantities of alkaloid compounds, none of which have been documented as the active ingredient for causing a decrease or cessation of the desire to use tobacco. Furthermore by containing *Hypericum perforatum*, the composition of the present invention provides an all natural anti-depressive property to counter the depression that is commonly associated with nicotine withdrawal; and therefore, by countering this important factor, one major difficulty of nicotine withdrawal is alleviated without the side effects associated with pharmaceutical anti-depressives and the likelihood of cessation from tobacco products is increased.

DESCRIPTION OF THE PREFERRED EMBODIMENT

The composition of the present invention comprises a *Plantago major* component and a *Hypericum perforatum* component and serves as an aid in smoking cessation. The herbs used in the present invention may by prepared for use either by a drying method or by an extraction method.

When a drying method is preferred, the herbs *Plantago major* and *Hypericum perforatum* are prepared by drying the herbs by suitable methods known in the art. After the herbs have been effectively dried, the entire plant or a portion thereof may be used in the composition of the present invention. When dried herbs are used in the present composition, the *Plantago major* component comprises from about 5% to about 95% by weight of the total composition and the *Hypericum perforatum* component comprises from about 95% to about 5% by weight of the total composition, wherein the dried *Hypericum perforatum* is standardized to comprise 0.3% by weight of Hypericin, which is one of the active constituents in *Hypericum perforatum*. Dried *Plantago major* and *Hypericum perforatum* are commercially available from Natures Value, Bayshore, N.Y. Alternatively, the *Plantago major* and *Hypericum perforatum* for use in the composition of the present invention may be prepared as liquid extracts of the herbs by extraction methods known in the art. The herbs may be extracted in either alcohol and water or by a glycerin and water based extraction method. One preferred extraction method comprises preparing the extracts of the herbs by a maceration process involving an alcohol (ethanol, ethyl alcohol, and not methanol) treatment, as is known in the art. Alternatively, the glycerin and water extraction process is particularly useful because glycerin may be used as a solvent in a liquid core of a capsule. Liquid filtrate which is obtained in a conventional extraction process after filtering the extractant liquid may then be further refined by removing any solvents with sufficiently low boiling points such as an alcohol by using standard evaporation techniques until the composition is substantially free from such solvents. Stabilizers and preservatives are typically added during the extraction method. When the *Plantago major* and *Hypericum perforatum* are prepared using extraction methods, the composition of the present invention comprises *Plantago major* extract in the amount from about 0.05% to about 40% by volume of the total composition and *Hypericum perforatum* extract in the amount from about 0.05% to about 40% by volume of the total composition, wherein the *Hypericum perforatum* extract is standardized to comprise 0.3% Hypericin. *Plantago major* and *Hypericum perforatum* extracts are commercially available from BioBotanical Laboratories, Inc., Ferndale, Wash.

In accordance with the present invention, once the *Plantago major* and *Hypericum perforatum* components have been prepared for use in the composition of the present invention by either a drying process or by an extraction process, the *Plantago major* and *Hypericum perforatum* components may be used in a composition which is intended to be orally ingested. Suitable compositional forms which may be administered orally include but are not limited to soft and hard gelatin capsules, pills, coated pills, tablets, dragees, and other forms known in the art.

When the *Plantago major* and *Hypericum perforatum* composition is to be administered in a soft or hard gelatin capsule form, a liquid core component is prepared and then encapsulated in a soft or hard gelatin shell in accordance with the present invention. As is known in the art, preselected amounts of pharmaceutical or herbal compositions can be encapsulated within soft or hard gelatin shells. When using soft gelatin shells, the soft gelatin shells typically comprise gelatin, plasticizers, water and other compositions. Gelatin is an essential component of the soft gelatin shells and conventionally one or more plasticizers are incorporated to produce a soft gelatin shell. The soft gelatin thus obtained has the required flexibility characteristics for use as an encapsulating agent. Useful plasticizers include glycerin, sorbitan, sorbitol, or similar low molecular weight polyols, and mixtures thereof. A preferred plasticizer is glycerin. The soft gelatin shells also comprise water. Without being limited to theory, water is believed to aid in the rapid dissolution or rupture of the soft gelatin shell upon contact with the gastrointestinal fluids encountered in the body. The shell may contain still other usual accessory substances, such as preservatives or coloring substances and pigments.

As is generally known in the art, the production of soft gelatin capsules comprises a first operation by which a wet capsule is formed and which is thereafter dried. Accordingly, the gelatin used for making the shell of the capsule contains at the time of manufacture a considerable proportion of water. During drying of the capsules, the water contained in the walls of the wet capsule normally does not completely vaporize. A small proportion of the water passes into the liquid core.

The liquid core of the soft gelatin capsules for use in the present invention comprises the *Plantago major* component and the *Hypericum perforatum* component along with conventional stabilizers, preservatives and other components known in the art. The liquid core has a sufficient quantity of solvent to act as a carrier of the *Plantago major* component and *Hypericum perforatum* component. In accordance with the present invention, the *Plantago major* component and *Hypericum perforatum* component may be added to the liquid core in either a dried state or as an extract. The upper limit of the addition of the *Plantago major* and *Hypericum perforatum* to the liquid core lies in the solubility of the herbs in the solvent. Conventional liquid core solvents include but are not limited to polyethylene glycols, polyvinylpyrrolidone, propylene glycol, and glycerol. The liquid core may also comprise a mixture of ethanol and one or more partial glycerides of fatty acids having from 6–18 carbon atoms. The partial glycerides useful in the liquid core include monoglycerides or diglycerides as well as mixtures thereof, e.g., See U.S. Pat. No. 4,888,239 to Brox, which is incorporated by reference herein in its entirety. Other components which can be incorporated into the liquid core include colorings, flavorings, preservatives, lubricants, flow-enhancers, filling aids, anti-oxidants, essences, and other aesthetically pleasing components. A preferred preservative for use in the liquid core of the present invention is citric acid.

When a soft gelatin capsule is the preferred means of administering the *Plantago major* and *Hypericum perforatum* composition of the present invention, the *Plantago major* and *Hypericum perforatum* components are preferably prepared as liquid extracts for use in the liquid core of a capsule. As hereinbefore recited, standard extraction methods, including alcohol and water or glycerin and water, may be used to prepare extracts of *Plantago major* and *Hypericum perforatum*.

Any suitable soft gelatin capsule known in the art may be used with the *Plantago major* and *Hypericum perforatum* composition of the present invention. For example, soft gelatin capsules are disclosed in U.S. Pat. No. 4,744,988; U.S. Pat. No. 5,431,916; and U.S. Pat. No. 5,641,512, all of which have hereinbefore been incorporated by reference in their entirety. Suitable soft gelatin capsules for use in the present invention are soluble in water and in gastrointestinal fluids. Upon swallowing the capsule, the gelatin shell rapidly dissolves or ruptures in the gastrointestinal tract thereby introducing the *Plantago major* and *Hypericum perforatum* composition from the liquid core into the physiological system.

In accordance with the present invention, the *Plantago major* and *Hypericum perforatum* composition may be orally ingested in a pill form. Conventional pelletizing methods may be used to manufacture the *Plantago major* and *Hypericum perforatum* composition in pill form. As is known in the pharmaceutical arts and in other arts, the components may be weighed, blended and pelletized to form a solid pill form. In addition, tablets may be prepared according to a dry or wet granulating procedure as is known in the art. These solid forms, e.g., pill, may be orally ingested and upon swallowing, they rapidly dissolves in the gastrointestinal tract thereby introducing the active material within the pill into the physiological system. In accordance with the present invention, the *Plantago major* and *Hypericum perforatum* herbs may be incorporated and pelletized in a dried state or a liquid extract of the herbs may be prepared before the extract solvent is evaporated using conventional techniques thereby leaving a solid extract residue. This solid extract residue may then by weighed and blended into a pill form along with suitable solid carrier materials. When dried herbs are used as a material to be pelletized into a pill, the entire dried plant or a portion thereof may be used. Preferably, the *Plantago major* comprises between about 5% to about 95% by weight of the total composition and the

*Hypericum perforatum* also comprises between about 95% to about 5% by weight of the total composition.

The *Plantago major* and *Hypericum perforatum* composition of the present invention offers significant advantages over prior art tobacco cessation products. The composition of the present invention is easily orally ingested in either a capsule form or a pill form. The composition of the present invention combines the desirable properties of *Plantago major* and *Hypericum perforatum* in one product for aiding in the cessation of tobacco use. *Plantago major* is an all natural herb which creates an aversion to tobacco and eases anxiety. Therefore, the danger of increasing the nicotine addiction inherent in the use of nicotine patches is avoided with this invention. *Hypericum perforatum* is an all natural herb which acts as an anti-depressive and advantageously has very few side effects, unlike the pharmaceutical composition bupropion which is often dispensed as an anti-depressive to help with the depressive effects of nicotine withdrawal. Because the depressive effects associated with nicotine withdrawal are an important factor in nicotine addiction, the use of the herb *Hypericum perforatum* in the composition aids in diminishing the desire for tobacco products.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A method for aiding an individual in the cessation of tobacco use, comprising the steps of:

administering to the individual a composition containing a *Plantago major* component and a *Hypericum perforatum* component, said *Plantago major* component and said *Hypericum perforatum* component being present in said composition in an amount effective to cause an aversion to tobacco;

wherein said composition is administered orally.

2. The method of claim 1, wherein said composition is in the form of a tablet, capsule, pill, coated pill or dragee.

3. The method of claim 1, wherein said *Plantago major* and *Hypericum perforatum* components are prepared either by drying *Plantago major* and *Hypericum perforatum* plants or by preparing an extract from *Plantago major* and *Hypericum perforatum* in an amount effective to cause an aversion to tobacco.

* * * * *